(12) United States Patent
Palleschi et al.

(10) Patent No.: US 6,657,721 B1
(45) Date of Patent: Dec. 2, 2003

(54) METHOD FOR QUANTITATIVE ANALYSIS OF ATOMIC COMPONENTS OF MATERIALS BY LIBS SPECTROSCOPY MEASUREMENTS

(75) Inventors: Vincenzo Palleschi, Pisa (IT);
Elisabeth Tognoni, Pisa (IT);
Allesandro Ciucci, Livorno (IT);
Simone Rastelli, Massa e Cozzile (IT)

(73) Assignee: Consiglio Nazionale Delle Richerche, Rome (IT)

( * ) Notice: Subject to any disclaimer, the term of this patent is extended or adjusted under 35 U.S.C. 154(b) by 0 days.

(21) Appl. No.: 09/646,608
(22) PCT Filed: Mar. 18, 1999
(86) PCT No.: PCT/EP99/01842
§ 371 (c)(1),
(2), (4) Date: Sep. 20, 2000
(87) PCT Pub. No.: WO99/49301
PCT Pub. Date: Sep. 30, 1999
(Under 37 CFR 1.47)

(30) Foreign Application Priority Data
Mar. 20, 1998 (IT) .......................................... PI98A0023

(51) Int. Cl.$^7$ ......................... G01N 21/63; G01N 21/71
(52) U.S. Cl. ...................................................... 356/318
(58) Field of Search .................................. 356/317, 318

(56) References Cited
FOREIGN PATENT DOCUMENTS
WO    WO 97/15811 A    5/1997

OTHER PUBLICATIONS

Goodard B J: "Materials analysis using laser-based spectroscopic techniques" Transactions of the Institute of Measurement and Control, 1991, UK, vol. 13, No. 3, pp. 128–139.

Song K et al: "Applications of Laser-Induced Breakdown Spectrometry" Applied Spectroscopy Reviews, vol. 32, No. 3, Aug. 1997, pp. 183–235.

*Primary Examiner*—F. L. Evans
(74) *Attorney, Agent, or Firm*—Nixon & Vanderhye, P.C.

(57) ABSTRACT

A method based on the LIBS technique is described, which allows to determine, without calibration of the measurement system, the concentration of atomic components in solid, liquid and aerial samples. The method comprises: (a) obtaining the plasma temperature (T) of at least one species of the emitted radiation; (b) determining the partition function U (T) of each species of the emitted radiation at the plasma temperature; (c) calculating the concentration value of each species once deducted an experimental factor (F); (d) calculating the concentration value of each non-individuated species by Saha equation; (e) calculating the concentration of atomic components as sum of the corresponding species concentrations; (f) measurement of the concentration of components by eliminating the experimental factor through normalization.

15 Claims, 4 Drawing Sheets

Determination of the working regime:
a) energy of the laser pulse and repetition rate;
b) focusing and receiving optics;
c) delay and duration of the acquisition gate;
d) spectrometer set up Spectra Acquisition at fixed working spot Spectra Analysis:
a) individuation of the lines;
b) measurement of the wavelength at mid line;
c) measurement of the line integral Qualitative analysis:
identification of the species through correspondence between the measurement at mid line and proper database, according to the maximum probability criterion.

Quantitive analysis:
a) calculation of the temperature T on at least one species;
b) calculation of the partition function of each species;
c) calculation of the concentration of the species times the experimental factor F;
d) calculation of the concentration of the species that have not been individuated by Saha equation;
e) calculation of the concentration of the elements as a sum of the concentrations of the species;
f) measurement of the concentration of the elements through elimination of the F factor by means of normalization or internal reference.

Fig.7

METHOD FOR QUANTITATIVE ANALYSIS OF ATOMIC COMPONENTS OF MATERIALS BY LIBS SPECTROSCOPY MEASUREMENTS

BACKGROUND

I. Field of the Invention

The present invention relates to a method for quantitative analysis of atomic components of materials by LIBS spectroscopy measurements without calibration.

II. Related Art and Other Considerations

Quantitative and real time analysis of the elementary composition of materials is of great interest in many fields, from industrial production to environment diagnostics, from on-line control of product quality to monitoring of industrial exhaust.

At present, the most widespread systems of quantitative analysis require sampling of the materials, with a consequent off-line characterisation. Generally, this procedure involves an increase of the times for the acquisition of the necessary data and, therefore, of costs and risks.

The LIBS (Laser Induced Breakdown Spectroscopy) or LIPS (Laser Induced Plasma Spectroscopy) technique is a technique for quick analysis of a sample's elementary constituents, that can be applied in situ and gives results in real time. Current systems based on LIBS rely on calibration curves in order to determine the concentration of the various elements [D. A. Cremers, M. J. Ferris and M. Davies: *"Transportable Laser Induced Breakdown Spectroscopy (LIBS) instrument for field-based soil analysis"*. SPIE Vol. 2835 (190–200) 1996].

BRIEF SUMMARY

The present invention proposes a method based on LIBS technology for determining the concentration of the various elements present in the sample, without use of calibration curves.

The method of the present invention and embodiments thereof are defined in the claims.

The application of the present method allows:

i) to perform quantitative analysis by the LIBS technique, without need of reference samples, and without calibrations;

<The article of B. J. Goddard "Materials analysis using laser-based spectroscopic techniques", Transaction of the Institute of Measurement an Control, 1991, UK, vol. 13, no. 3, pages 128–139, discloses several laser based spectroscopic methods capable of detecting low concentrations of a particular element. In the case of a LIBS methods, for a system in LTE it is possible to derive the relative concentrations of the elemental constituents by measuring line intensities,>

<<The patent application WO 97/15811 relates to spectroscopic determination of the concentration of atomic species in samples. The concentration of the atomic species to be determined is then derived from the known emission intensity of a predetermined concentration of that specie in the sample at the measured temperature, a quantity which would have been measured prior to the determination of the unknown concentration, and the actual measured emission from the unknown species, or by this latter emission and the emission intensity of a species having known concentration within the sample such as nitrogen for gaseous air samples,>> ii) to reduce measurement costs and times, because the method is self-consistent (the experimental quantities that are necessary to determine the concentrations are absolute quantities that are obtained from the same measure).

BRIEF DESCRIPTION OF THE DRAWINGS

FIG. 7 is a block diagram depicting generally a procedure for quantitative analysis.

DESCRIPTION

Figure 1:
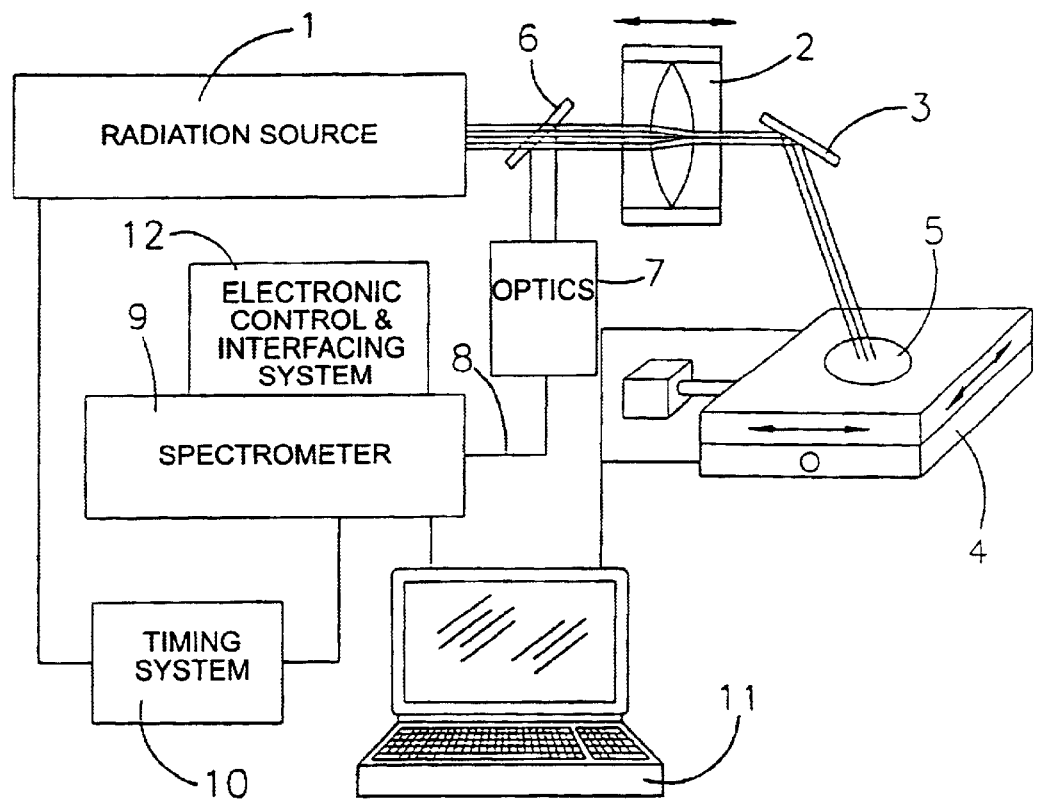
FIG. 1 is a schematic view of apparatus for performing analysis of an object.

The invention is described herein, with illustrative and non-limiting purpose, for some applications that are considered as being particularly significant.

a) Working Principle of the LIBS Technique

LIBS is based on the analysis of the spectrum of the radiation emitted by the atoms of the sample, when they are excited and ionised by a laser pulse that is properly focused on the target.

The beam of a pulsed laser is focused on a sample through an appropriate optical system. If the energy of the laser pulse is sufficiently high, the density of photons in the focal spot is such as to trigger multiphotonic ionisation (even if the phenomenon has a very low probability). The first free electrons are accelerated by the electric field of the radiation and they ionise other atoms by impact; a chain reaction which produces the breakdown, with its characteristic detonation noise and flash of light, is thus generated. The plasma (composed of neutral atoms, ions and free electrons), which is formed in the first instants of the laser pulse, absorbs energy from the laser pulse, thus reaching temperatures of the order of about ten eV ($\sim 10^5$ K)($\sim 10^7$° C.). The material contained in the focal spot (characteristic volume $\sim 0.1$ mm$^3$) is thus heated and ionised. Once the pulse and heating phase are over, the plasma cools down and the atomic species generate their specific spectrum. By resolving the evolution of plasma through time, it is possible to discriminate various radiation regimes;

a) bremsstrahlung radiation;

b) emission of the spectrum lines of the elements;

c) emission of vibration bands of simple molecules, formed as a consequence of the impacts.

LIBS analysis is based on the measurement of the lines indicated at point b). To is purpose, the observation of the spectrum must start with a certain delay with respect to the laser pulse, in order to reduce the effects of the presence of bremsstrahlung radiation. The typical working regime thus individuated corresponds to plasma temperatures of the order of 1 eV ($\sim 10^4$° C.). The duration of the observation is established on the bases of the characteristics of the apparatus (energy and duration of the laser pulse) in order to maximise the signal/noise ratio and to limit the temperature variations due to the dynamics of plasma.

In the case in which during the time interval of observation the condition of LTE (*Local Thermal Equilibrium*),

["Principles of Laser Plasma" Ed. by G. Bekefi, J. Wiley & Sons, 1976] is verified, the plasma is characterised by its temperature and by the electronic density.

The atomic elements that form the plasma are present in different ionisation states. It is called species herein an element having a certain ionisation state (e.g.: neutral magnesium [MgI] and ionised magnesium [MgII] are two species of the same element). In the case of LTE, the population of the atomic levels is described by Boltzmann distribution; the ratio between populations of two levels belonging to subsequent ionisation states of a same element is given by Saha-Boltzmann equation:

$$\frac{N_e N_l(Z)}{N_n(Z-1)} = 6.0 \times 10^{21} \frac{g_l^Z T_e^{3/2}}{g_n^{Z-1}} \exp(E_\infty^Z(n,l)/T_e), \quad (1)$$

where:

$N_e$: electronic density (cm$^{-3}$);

$N_n$ (Z-1): level n population, of the species with (Z-1) charge;

$N_l(Z)$: fundamental level population, of the species with (Z) charge;

$g_l^Z$: degeneration of the fundamental level of the species with (Z) charge;

$g_n^{Z-1}$: degeneration of the n level of the species with (Z-1) charge;

$E_\infty^Z(n,l)$: ionisation energy of the (Z-1) charge species initially at level (n, l);

$T_e$: electronic temperature of plasma.

$T_e$, which appears in equation 1, is the temperature of the distribution of the free electrons in the plasma; while T plasma temperature stands for temperature of the bonded electrons. In working condition (LTE), the difference between these temperatures is negligible.

The intensity of each spectral line, characteristic of each species a present in the plasma, depends on the concentration of the same species $N_a$ and on the population of the starting level, that is on the plasma temperature T, according to the formula:

$$I_{ki}^\lambda = N_a \frac{g_k \exp(-E_k/k_B T)}{U_a(T)} A_{ki} \quad (2)$$

where $I_{ki}^\lambda$ is the number of photons emitted per volume unit and for time unit at the wavelength λ, characteristic of the transition between the levels k and i of the species a, $g_k$ is the degeneration of the upper level, $E_k$ the energy of the upper level, $k_B$ the Boltzmann constant, $A_{ki}$ the probability of transition between the two levels k and i, $U_a(T)$ the partition function of the species a at the temperature T, according to the expression:

$$U_a(T) = \sum_k g_k \exp(-E_k/k_B T) \quad (3)$$

b) Procedure for the Analysis at the Base of the Proposed Method

The value of the quantity T is obtained through measurements of the intensity of the radiation emitted by electronic transitions.

The measured intensity values, $\bar{I}_{ki}^\lambda$, are connected with the emitted intensity, $I_{ki}^\lambda$, by a proportion factor F, depending on the experimental apparatus and on the measurement conditions (the spectral response of the experimental apparatus is evaluated in the calculation of the quantity $\bar{I}_{ki}^\lambda$).

Such factor F must be constant during a measurement run, that is the acquisition of all the portions of spectrum that are necessary to the measurement must be taken under the experimental conditions.

Therefore the following relation is valid:

$$\bar{I}_{ki}^\lambda = F I_{ki}^\lambda \quad (4)$$

By utilising the measured values of the intensity of the lines emitted by a same species and the relative spectroscopic data ($E_k$, $g_k$, $A_{ki}$, that are available in literature), it is possible to calculate the temperature of the plasma. By substituting in eq. 4 the expression $I_{ki}^\lambda$, from equation 2, and by taking the natural logarithm of both terms the result is:

$$\ln \frac{\bar{I}_{ki}^\lambda}{g_k A_{ki}} = \ln \frac{F N_a}{U_a(T)} - \frac{E_k}{k_B T} \quad (5)$$

In the LTE condition, the temperature T is the same for all species and $U_a(T)$ is determined by the temperature. Equation 5 is therefore the equation of a straight line:

$$y_{ki} = m + n x_{ki} \quad (6)$$

where; $x_{ki} = E_k$ $y_{ki} = \ln(\bar{I}_{ki}^\lambda / g_k A_{ki})$ $m = \ln(F N_a / U_a(T))$ $n = -1/k_B T$ For each species, the values ($x_{ki}$, $y_{ki}$) which characterise each line are reported on the plane (E, $\ln(\bar{I}/gA)$): for each species the value of the slope n and of the intercept m is obtained by linear regression. The slope n thus obtained gives the value of the temperature of the plasma:

$$T = -1/k_B n. \quad (7)$$

With the value T calculated through equation 7 (possibly averaged on the different species), the value of the $U_a(T)$ is determined through equation 3. At this point, by using the intercept value m, it i possible to calculate the value of the concentration $F N_a$, that is the product of the concentration of the species a times the experimental factor F.

In this way, one proceeds to the measurement of $F N_a$ for all the species that have been identified (Note: once T has been found, the measure of a single line will be sufficient to determine $F N_a$).

In working conditions (T~1 eV)(~10$^4$° C.) only spectra that are emitted by the first two species of each element, that is by the neutral state and by the first ionisation one, are observed: indeed, the relative abundance of atoms in states of ionisation above the first is lower than 10$^{-3}$.

Once the plasma temperature and the species concentrations (times the F Factor) have been obtained, the concentration of the elements (hereinafter indicated by $C_i$) can be calculated.

The procedure is done according to the following scheme:

A) Calculation of the Concentrations of the Elements Times the Experimental Factor F.

For each element the following cases can be encountered:

i) the concentrations $F N_a$ for both species are available: then the concentration of the element is obtained through the sum of the concentrations of the two species. In addition, through eq. 1, it is possible to calculate $N_e$ (that in this case is the only unknown quantity). Then, the procedure continues according to point B)

ii) the concentration for only one of the two species is available and the value $N_e$ is known (this case occurs when there is at least one element for which the concentrations of both species have been measured); the concentration of the element can be obtained by calculating the concentration of the other species, through eq. 1, and by summing the concentrations of the two species. Then, the procedure continues according to point B)

iii) the concentrations for only one of the two species is available and the value $N_e$ is not known (this case occurs when it is possible to measure the lines of a single species for each one of the identified element): in this case $N_e$ is calculated as value of convergence of an iterative algorithm based on Saha equation and on the concentrations of the species that have been individuated. That is, a reasonable starting value for $N_e$ must be set (in the typical working conditions $N_e \sim 10^{18}$ electrons/cm$^3$) and then the procedure continues according to point ii) for the determination of the concentrations of the elements, times the F factor; then it is necessary to proceed with the calculation of the real concentrations according to point B). Once the F factor has been eliminated and the concentrations of the elements have been obtained, $N_e$ is recalculated as the sum of the concentrations $N_i$ of the ionised species (for the neutrality condition of plasma this corresponds to:

$$N_e = \sum_{i=1}^{Tot} N_i(II),$$

where Tot is the number of individuated elements). This new value of $N_e$ is reintroduced at point iii) of the algorithm and the cycle is repeated until the value of $N_e$ converges.

B) Determination of the Experimental Factor F and Calculation of the Real Concentrations.

It is possible to proceed in two ways:

i) to utilise an internal reference. When the concentration $C_{element}^{known}$ of an element of the sample is known (e.i. Nitrogen in atmosphere), it is possible to determine the factor F as the ratio between the concentration of the same element, as measured with the LIBS method according to point A), and the known concentration $$F = \frac{(FC_{element})LIBS}{C_{element}^{known}}, \quad (8)$$

and then to rescale the other concentrations with the value F, thus determined;

ii) to normalise each concentration with respect to the sum of all concentrations:

$$C_i = \frac{(FC_i)_{LIBS}}{\sum_{j}^{Tot} (FC_j)_{LIBS}}, \quad (9)$$

where Tot indicates the number of individuated elements. The concentrations calculated according the methods described in point ii) are affected by a percentage error that is equal to at least the concentration of the elements that have not been individuated. The measurements taken according to the method described in point i) are affected only by a percentage error that is determined by the precision by which the reference is known, but such method is only applicable when an internal reference is available.

Figure 6:
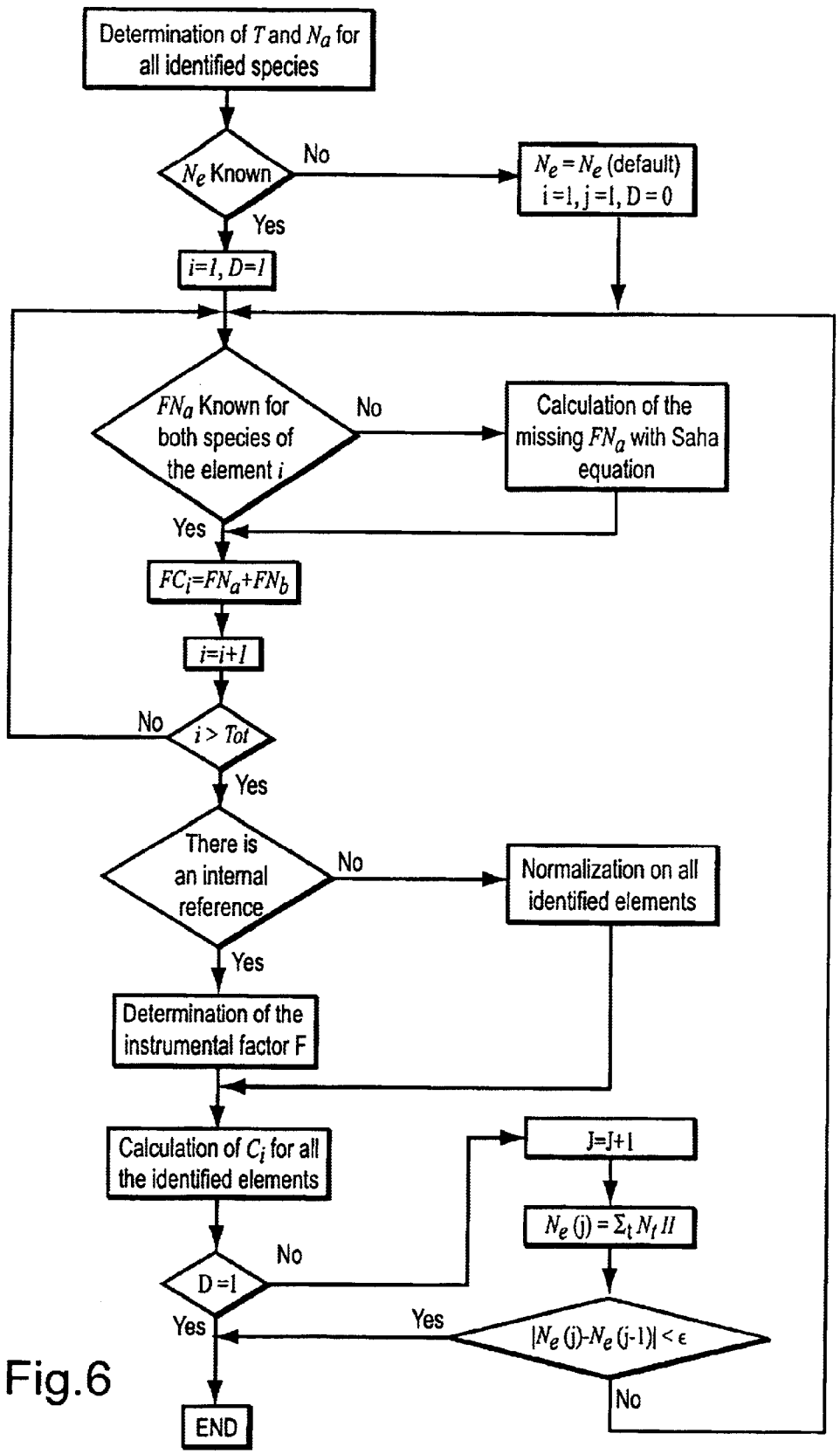
FIG. 6 is a flowchart showing basic steps involved in an analysis method according to a mode of the invention.

The algorithm described in points A) and B) is summarised in the flow chart shown in FIG. 6.

A block scheme describing the procedure for the quantitative analysis herein presented, is shown in FIG. 7.

Description of Possible Applications

There are described hereinafter different applications of the LIBS technique here described. In all applications the same spectrum analysis procedure that is described in the previous block scheme is utilised.

a) Characterisation of Metal Alloys

In the characterisation of metal alloys the interest is usually on the measurement of the concentration of the major components, that is of the components that are present in percentage that is at least 0.1%. In other cases it can otherwise be important to determine the presence of impurities in the alloys, in a quick way, giving priority to measurement sensitivity rather than accuracy.

A suitable apparatus is shown in FIG. 1 and consists of a laser radiation source 1, a focusing optic system 2, a first mirror 3, a support 4 for a metal alloy sample 5, a second mirror 6, an optic system 7 for receiving the emitted signal, an optic fibre 8, a spectrometer 9, a timing system 10 for discriminating the spectrum lines from the continuous emission, a computer 11, an electronic control and interfacing system 12 and a software for analysis of data.

For the analysis of metal alloys, typical working conditions are:

density of laser radiation flow on the target: $\sim 10^8$ Wcm$^{-2}$ repetition rate of 10 Hz reception with quartz optics (transparent to UV)

use of a system for the movement of the sample to control the irradiated spot.

b) Monitoring of Trace Elements in the Atmosphere

In the analysis of traces in the atmosphere the interest is on the measurement of pollutans or other elements that are present in the form of aerosol, submicrometric particulate or vapours, in quantities in the order of ppm.

Figure 2:
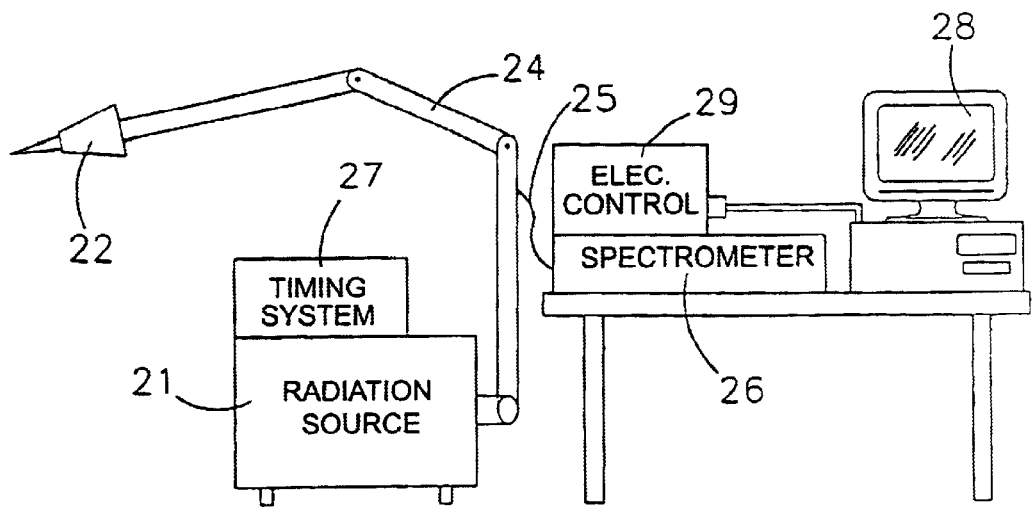
FIG. 2 is a schematic view of apparatus for performing analysis of atmosphere.

A suitable apparatus is shown in FIG. 2 and consists of a laser radiation source 21, a focusing optic system 22 for directing the laser radiation in the gas, an optic system 24, an optic fibre 25, a spectrometer 26, a timing system 27 for discriminating the spectrum lines from the continuous emission, a computer 28, an electronic control and interfacing system 29 and a software for analysis of data.

For the monitoring of the elements present in traces in the atmosphere, typical working conditions are:

density of laser radiation flow at the focal spot: $\sim 5.10^9$ Wcm$^{-2}$ repetition rate of 10 Hz (or greater)

reception with quartz optics (transparent to UV).

c) Analysis of Soils

Figure 3:
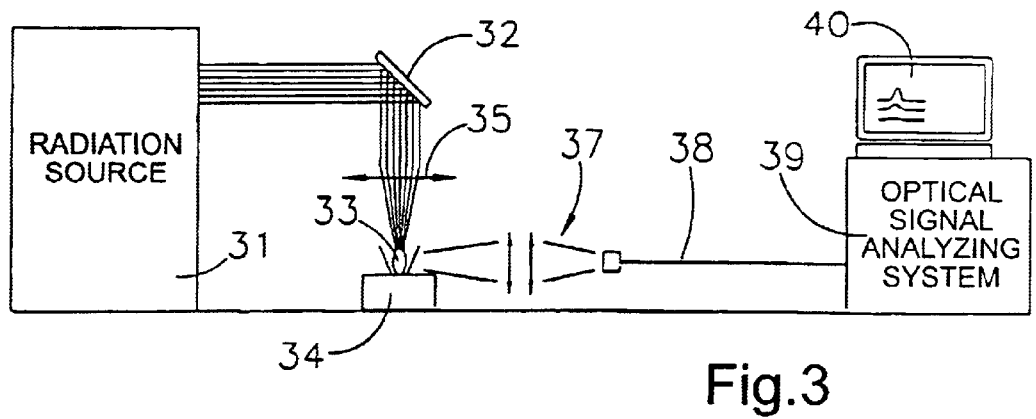
FIG. 3 is a schematic view of apparatus for performing analysis of soils.

A suitable apparatus for carrying out fast in situ or laboratory analysis of soils with the method according to the invention is shown in FIG. 3 and comprises a laser radiation source 31, a mirror 32 for directing the laser radiation towards on a soil sample 33 on a support 34, a focusing lens 35, a collecting optics 37, an otical fibre 38, an optical signal analysing system 39, a computer 40 and a software for analysis of data.

d) Analysis of Cultural Heritage

Figure 4:
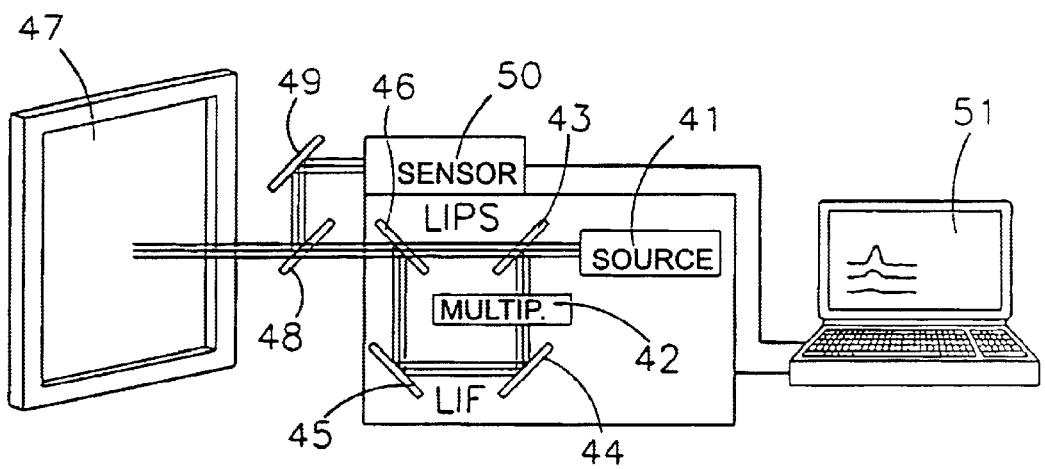
FIG. 4 is a schematic view of apparatus for performing analysis of cultural heritage.

A suitable apparatus for carrying out the analysis of cultural heritage with the method according to the invention is shown in FIG. 4 and comprises a laser radiation source 41, a frequency multiplier 42, a group of four mirrors 43–46 for selectively directing the laser radiation towards a target 47 either directly (LIPS analysis) or through a frequency multiplier [for LIF (Laser Induced Frequency) analysis], two further mirrors 48–49 for directing the emitted signsl towards a sensor 50, a computer 51 and a software for analysis of data.

e) Atomic Emission Spectroscopy

Figure 5:
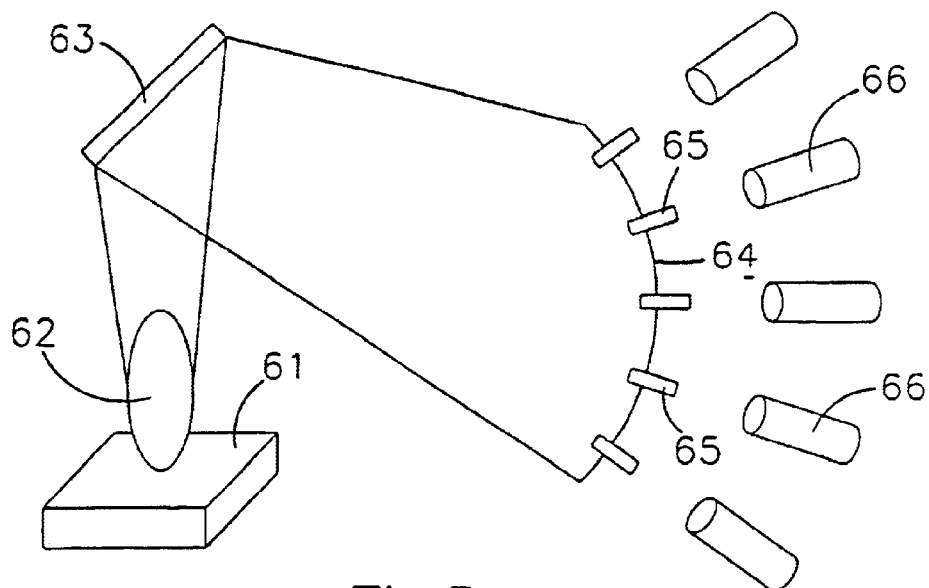
FIG. 5 is a schematic view of apparatus for performing analysis of atomic emission spectroscopy.

A suitable apparatus for carrying out atomic emission spectroscopy with the method according to the invention is shown in FIG. 5 and comprises a sample 61 on whose surface a plasma 62 is generated by a laser source or any other radiation source such as electric spark, microwaves and so on. The emitted signal reaches a dispersion reticule 63 inside a housing 64 provided with a plurality of slits 65, each faced to a respective photomultiplier 66. The photomultipliers collect the integral line intensity corresponding to specific emission lines of the materials, and these data are processed using the spectral analysis procedure here described.

What is claimed is:

1. A method for quantitative analysis of concentrations of atomic elements of a sample which has been excited and ionized in such a way to generate a plasma and to emit emitted radiation, the method being performed without calibration of the emitted radiation and comprising:
   a) measuring intensity of spectral lines emitted by each element;
   b) obtaining a plasma electron temperature (T) from at least one species of the emitted radiation;
   c) determining a concentration ($N_a$) of all the species multiplied by a proportion factor (F);
   d) calculating a concentration of each element as a sum of the corresponding species concentrations;
   e) normalizing the concentration of each element with respect to a sum of the concentrations of all the elements in order to eliminate said proportion factor (F).

2. The method according to claim 1, further comprising determining the temperature (T) by averaging measures of more than one species.

3. The method according to claim 1, further comprising determining the value of the electronic density ($N_e$).

4. The method according to claim 3, further comprising, if the concentration ($FN_\alpha$) for only one of the species is available, calculating the concentration of the other species using the Saha-Boltzmann equation.

5. The method according to claim 1, further comprising, if the concentration ($FN_\alpha$) for only one of the species is available and the value of an electronic density ($N_e$) is not known, calculating the concentration of the other species as a convergence value of an iterative algorithm based on Saha-Boltzmann equation and on the concentrations of species that have been individuated.

6. The method according to claim 4, wherein said iterative algorithm comprises:
   a) setting a starting value for the electronic density ($N_e$),
   b) calculating the concentration of the other species by means of the Saha-Bolzmann equation,
   c) normalizing each concentration with respect to the sum of the concentrations of all elements in order to eliminate said proportion factor (F),
   d) calculating the electronic density ($N_e$) as the sum of the concentrations ($N_i$) of the ionized species,
   e) reintroducing the value of the electronic density ($N_e$) in the calculation at the point b), and repeating the cycle until the value of the electronic density ($N_e$) converges.

7. The method according to claim 1, further comprising:
   a) individuating the spectral lines;
   b) measuring a wavelength at a mid line;
   c) measuring a line integral.

8. The method according to claim 1, further comprising identifying the species through correspondence between the wavelength measurement at mid line and proper database, according to a maximum probability criterion.

9. The method according to claim 1, wherein the sample comprises a metal alloy.

10. The method according to claim 1, wherein the sample comprises trace elements in the atmosphere.

11. The method according to claim 1, wherein the sample comprises soil.

12. The method according to claim 1, wherein the sample comprises cultural heritage.

13. The method according to claim 1, wherein the method utilizes atomic emission spectroscopy.

14. A system for quantitative analysis of atomic elements of a material by LIBS spectroscopy measurements, the system comprising:
   a) a laser radiation source;
   b) optical means to direct the laser radiation toward the material;
   c) an optic system for receiving the radiation emitted by the plasma generated by the material;
   d) an optical signal analysing system;
   e) a computer which performs the followings steps:
      measuring intensity of spectral lines emitted by each element:
      obtaining a plasma electron temperature (T) from at least one species of the emitted radiation;
      determining a concentration ($N_e$) of all the species multiplied by a proportion factor (F);
      calculating a concentration of each element as a sum of the corresponding species concentrations;
      normalizing the concentration of each element with respect to a sum of the concentrations of all the elements in order to eliminate said proportion factor (F).

15. A software program comprising instructions stored in a memory and executable by a computer for performing quantitative analysis of concentrations of atomic elements of a sample which has been excited and ionized in such a way to generate a plasma and to emit emitted radiation, and wherein upon execution the program performs the steps of:
   measuring intensity of spectral lines emitted by each element:
   obtaining a plasma electron temperature (T) from at least one species of the emitted radiation;
   determining a concentration ($N_e$) of all the species multiplied by a proportion factor (F);
   calculating a concentration of each element as a sum of the corresponding species concentrations; and
   normalizing the concentration of each element with respect to a sum of the concentrations of all the elements in order to eliminate said proportion factor (F).

* * * * *